United States Patent [19]

Gutowski et al.

[11] 4,029,663

[45] June 14, 1977

[54] DIMERIC ANHYDRO-VINCA DERIVATIVES

[75] Inventors: Gerald E. Gutowski; Jean C. Miller, both of Indianapolis, Ind.

[73] Assignee: Eli Lilly and Company, Indianapolis, Ind.

[22] Filed: July 10, 1975

[21] Appl. No.: 594,915

[52] U.S. Cl. .............................. 260/287 B; 424/262
[51] Int. Cl.² ...................................... C07D 519/04
[58] Field of Search ................................ 260/287 B

[56] References Cited

UNITED STATES PATENTS

| 3,097,137 | 7/1963 | Beer et al. | 260/287 B |
| 3,352,868 | 11/1967 | Neuss et al. | 260/287 B |

OTHER PUBLICATIONS

"Cancer Chemotherapy Reports," vol. 1, pp. 9–18 (1959).

*Primary Examiner*—Donald G. Daus
*Assistant Examiner*—David E. Wheeler
*Attorney, Agent, or Firm*—James L. Rowe; Everet F. Smith

[57] ABSTRACT

Dimeric Vinca alkaloids are converted to three separable anhydro derivatives, useful as mitotic inhibitors or as intermediates for the preparation of other oncogenetically active alkaloids.

8 Claims, No Drawings

DIMERIC ANHYDRO-VINCA DERIVATIVES

BACKGROUND OF THE INVENTION

Several naturally-occurring alkaloids obtainable from *Vinca rosea* have been found active in the tratment of experimental malignancies in animals. Among these are leurosine (U.S. Pat. No. 3,370,057), vincaleukoblastine (vinblastine) to be referred to hereinafter as VLB (U.S. Pat. No. 3,097,137), leurosidine (vinrosidine) and leurocristine (VCR or vincristine) (both in U.S. Pat. No. 3,205,220). Two of these alkaloids, VLB and vincristine are now marketed as drugs for the treatment of malignancies, particularly the leukemias and related diseases in humans. Of these marketed compounds, vincristine is a most active and useful agent in the treatment of leukemias but is also the least abundant of the anti-neoplastic alkaloids of *Vinca rosea*. It is most desirable to increase the supply of vincristine, either by recovering more of the compound in the extraction process from Vinca leaves (see South African patent 72/8534), or by converting more abundant dimeric Vinca alkaloids, such as VLB, by chemical or biological methods to vincristine (see South African Pat. No. 72/8534). In addition, there is also the possibility of converting a less active alkaloid to VLB which can in turn be oxidized to vincristine.

The three most active naturally-occurring, antineoplastic alkaloids from Vinca rosea, VLB, vincristine and leurosidine, can be represented by the following formula:

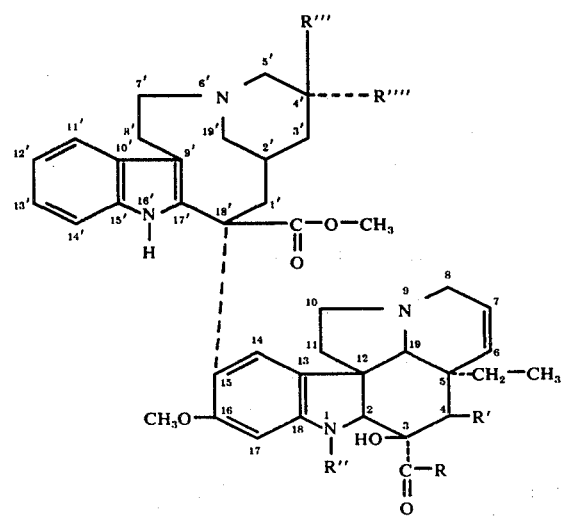

In VLB, R is methoxy, R' is acetoxy, R" is methyl, R'" is hydroxyl and R"" is ethyl. In leurosidine, R, R' and R" are the same as in VLB but the configuration at C-4' is reversed; i.e., R'" is ethyl and R"" is hydroxyl. In vincristine, R, R', R'" and R"" are the same as in VLB but R" is formyl. Another dimeric indole alkaloid useful as an intermediate is des-N-methyl VLB (also known as des-N-formylvincristine) with the same substituents as either VLB or vincristine except that R" is H. Des-N-methyl VLB is conveniently prepared by deformylation of vincristine.

Chemical modification of the Vinca alkaloids has been rather limited. In the first place, the molecular structures involved are extremely complex and chemical reactions which affect a specific function of the molecule are difficult to develop. Secondly, alkaloids lacking desirable chemotherapeutic properties have been recovered from *Vinca rosea* fractions, and a determination of their structures has led to the conclusion that these compounds are closely related to the active alkaloids. Thus, anti-neoplastic activity seems to be limited to very specific structures, and the chances of obtaining more active drugs by modification of these structures would seem to be correspondingly slight. Among the successful modifications of physiologically-active alkaloids has been hydrogenation of the $\Delta^6$ double bond — dihydro VLB (U.S. Pat. No. 3,352,868) — and the replacement of the acetyl group at C-4 (carbon no. 4 of the VLB ring system — see the numbered structure below) with a higher alkanoyl group or with unrelated acyl groups (see U.S. Pat. No. 3,392,173). Several of these derivatives are capable of prolonging the life of mice inoculated with P1534 leukemia. One of the derivatives in which a chloracetyl group replaced the C-4 acetyl group of VLB was also a useful intermediate for the preparation of structurally modified VLB compounds in which an N,N-dialkylglycyl group replaced the C-4 acetyl group of VLB (see U.S. Pat. No. 3,387,001).

Another recent modification of the indole-dihydro indole alkaloid structure has been the preparation of C-3 carboxamides and hydrazides of VLB, vincristine, leurosidine and their C-4 desacetyl derivatives (see Belgian Pat. No. 813,168, granted Oct. 2, 1974).

Atta-ur-Rahman, Pakistan J. Sci. Ind. Res., 14, 487 (1971) stated that he had prepared 3',4'-anhydro VLB by the condensation of carbomethoxy chlorocleavamine and vindoline.However, Kutney et al., Heterocycles, 3, 205 (1975) have demonstrated conclusively that the condensation product was, in fact, 18'-epi-3',-4'-dehydro VLB, processing the non-natural VLB stereochemistry at C-18'. Authentic 3',4'-anhydro VLB derivatives possessing the "natural" configuration at C-18' are not described elsewhere in the art.

It is an object of this invention to provide a series of new dimeric indole-dihydroindole alkaloids showing activity against experimental tumors in mice such as Ridgeway osteogenic Sarcoma and Gardner lymphosarcoma or as intermediates for the preparation of other anti-neoplastically active compounds.

SUMMARY OF THE INVENTION

In fulfillment of the above and other objects, this invention provides anhydro-Vinca alkaloids of the following structure:

-continued

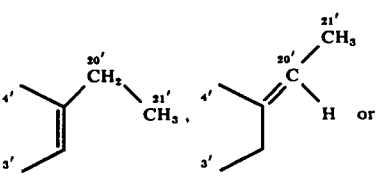

wherein R is OCH₃, NH₂, NHCH₃, NHC₂H₅, NH-C₂H₄OH or NH-NH₂; R'' is CH₃, H, or formyl; R' is hydroxy or acetoxy and Z is

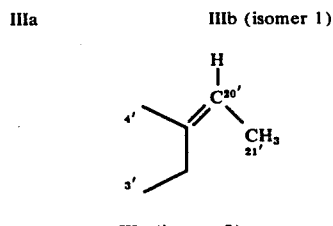

In the part formulae for "Z", the numbering for the 3' and 4' carbon atoms of the unmodified dimeric alkaloid ring system (see Formula I) plus the numbering for the 4'-ethyl group— 20' and 21'— have been included in order to indicate unambiguously the points of attachment of the free bonds of the part formulae.

Compounds according to the above formula are prepared by contacting a compound according to Formula I above in which one of R''' and R'''' is hydroxyl and the other is ethyl and R, R' and R'' are as defined above for Formula II with cold concentrated sulfuric acid. The reaction is carried out customarily by adding, with stirring, a starting material according to Formula I as defined in the form of a solid, either as the free base or as an acid addition salt, to a cold, concentrated (18M) sulfuric acid. The solid starting material is added to such a rate as to allow solution to take place rapidly. After the addition of the solid dimeric alkaloid had been completed, the reaction mixture is stirred for an additional period of time, usually less than one-half hour, and the product, a mixture of three anhydro compounds according to Formula II, is then isolated by adding methanol, neutralizing the sulfuric acid, and isolating the free base. The free base mixture thus obtained is separated by procedures well known in the art as by chromatography, recrystallization and the like into its components.

While compounds in which R is NH-C₂H₄OH can be prepared by the above procedure, they are preferably prepared by using an acid-stable hydroxyl protecting group during the sulfuric acid dehydration procedure and then removing the protecting group by standard methods as by basic hydrolysis or reductive methods (see McOmie—Protective Groups in Organic Chemistry—Plenum Press, New York, New York—1973). Alternatively, the three anhydro 4-desacetyl VLB C-3 carboxyhydrazides can be prepared by the sulfuric acid dehydration procedure from VLB C-3 carboxyhydrazide, each hydrazide converted to the corresponding azide with nitrous acid and the azide reacted with ethanolamine to give to desired anhydro 4-desacetyl VLB C-3 N-(2-hydroxyethyl)carboxamide.

The product of this sulfuric acid treatment contains three anhydro derivatives corresponding to Formula II above, one for each of the part structures for "Z". The part structure for "Z" designated as IIIa is also named as a 3',4'-anhydro VLB or vincristine derivative or the like and the part structures IIIb and IIIc are designated as isomeric 4',20'-anhydro derivatives, specifically isomer 1 and isomer 2. This isomerism, as can be seen by an inspection of the IIb and IIc part formulas, is due to cis-trans isomerism in that the methyl group at C-20' can be adjacent or remote to the nitogen at 6'. Based upon evidence of the NMR spectra, it is believed that compounds of the series in which Z is IIIb are most probably represented by

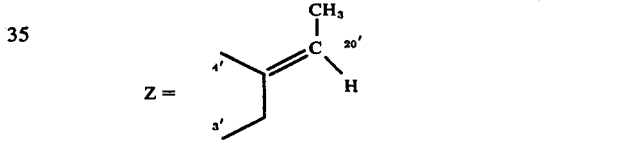

while compounds of the series in which Z is IIIc are most probably represented by

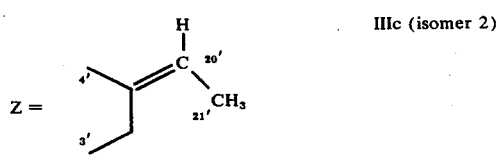

During the course of the above reaction or during the procedures used to isolate and separate the three anhydro derivatives, the acetoxy group at C-4, if present initially, is usually hydrolyzed to a hydroxy group to provide the same series of compounds as those prepared from a starting material having a hydroxy at C-4 initially. Reacetylation to prepare a C-4 acetyl (R' is acetoxy) is accomplished by following the procedure of Hargrove, Lloydia, 27, 340 (1964).

The preparation of compounds according to Formula II above is further illustrated by the following specific examples.

EXAMPLE 1

ANHYDRO COMPOUNDS FROM VINCRISTINE SULFATE 147.6 mg. of vincristine sulfate were slowly added to 877.1 mg. of cold 18M sulfuric acid. After the addition had been completed, the reacton mixture was stirred (at ambient temperature) for one-half hour. 13 ml. of dry methanol were then added followed by 2.8193 g. of solid sodium carbonate. The resulting mixture was stirred for about 45 minutes. 40 ml. of saturated aqueous sodium chloride were then added, and the volume made up to 80 ml. with distilled water. The resulting aqueous solution was extracted four times with equal volumes of benzene. The benzene extracts were separated, combined, dried and the benzene removed by evaporation. A residue weighing 57.2 mg. was obtained containing a mixture of three anhydro derivatives shown as three separate spots on thin layer chromatography. The reaction mixture was separated by preparative thin layer chromatography on silica gel using methanol as the eluant. The preparative chromatogram was divided into three zones manually and the anhydro derivative in each zone removed from the silica adsorbent by two washed with an ethyl acetate-methylene dichloride solvent mixture followed by two washes with methanol. The mixture of three anhydro compounds obtained from vincristine by the above reaction was thus separated and purified. During the sulfuric acid treatment and subsequent isolation procedures, the C-4 acetyl group hydrolyzed and the resulting anhydro derivatives were all derivatives of C-4 desacetyl vincristine. Each of these compounds had the structure of Formula II above in which R is methoxy, R' is hydroxy and R'' is formyl. 19.2 mg. of the 3',4'-isomer (Z is IIIa) were obtained having the following physical characteristics: Mass spectrograph: Molecular ion at 764, other peaks at 750, 736, 688, 676, 660, 554, 537, 494, 478, 336, 337, 279, 261, 247, 249, 219, 167, 149, 136, 120, 121, 111, 106 and a transmethylation peak at 778. (Partial) NMR spectrum (in deuterated chloroform) δ's (ppm) at 0.96, 3.58, 3.63, 3.74, 3.81, 3.87, and 5.41 (multiplet).

12.5 mg. of 4',20' ahydro C-4-desacetyl vincristine-isomer 1 (Z is IIIb) were obtained with the following characteristic mass spectrograph: molecular ion at 764, other ion peaks at 734, 704, 705, 706, 688, 660, 646, 630, 601, 602, 576, 488, 472, 368, 351, 337, 293, 279, 223, 167, 149, 123, 111, and a transmethylation peak at 778, and (Partial) NMR (CDCl$_3$) spectrum γ's at .94 (triplet), 1.65 (doublet), 3.58, 3.63, 3.75, 3.82, 3.88, 5.46 (multiplet).

8.7 mg. of 4',2'-anhydro C-4-desacetyl vincristine derivative, designated as isomer 2 (Z is IIIc) were obtained with the following mass spectrograph: molecular ion at 764 and other ion peaks at 736, 705, 677, 606, 413, 368, 351, 336, 337, 313, 279, 167, 149, 121, 111 and a transmethylation peak at 778, and (Partial) NMR (CDCl$_3$) spectrum γ's at 0.90 (triplet), 1.71 (doublet), 3.59, 3.64, 3.75, 3.82, 3.86, and 5.30 (multiplet).

EXAMPLE 2

ANHYDRO COMPOUNDS FROM VLB SULFATE

Following the procedure of Example 1, 560 mg. of VLB sulfate were added gradually with stirring to 2.9681 g. of cold 18M sulfuric acid. The reaction was carried out and the mixture of the three anhydro C-4-desacetyl VLB derivatives (compounds according to Formula II above in which R is methoxy, R' is hydroxy, R'' is methyl and Z is as defined (IIIa—c) were isolated by the procedure of that example. The three anhydro derivatives were separated by preparative thin layer chromatography, the band corresponding to each derivative was removed manually and the compound washed therefrom with methanol. Fractions were obtained having a total weight of 162.4 mg. (35 percent yield). Fractions corresponding to the two isomeric 4',2'-anhydro derivatives were shown by thin layer chromatography to be impure and these two fractions were separately placed on preparative thin layer chromatographic plates and rechromatographed. Final yields of purified material were as follows: 3',4'-anhydro C-4-desacetyl VLB (Z is IIIa), 55.3 mg. with the following physical characteristics: NMR spectrum (in deuterated chloroform) γ's (ppm) at 1.00,~2.00 (multiplet), 3.75 (N-methyl), 3.60, 3.81, 3.85, 4.10, 5.46 (multiplet), 5.80 (ethylenic hydrogens), 6.11, 6.61. Mass spectrograph: Molecular ion at 750; other peaks at 570, 427, 240, 188, 152, 136, 135, 122, 121, 107, 106, and transmethylation peaks at 764 and 778.

4'-20'-Anhydro C-4 desacetyl-VLB isomer 1 (Z is IIIb) 41.4 mg. with the following physical characteristics: (Partial) NMR spectrum (deuterated chloroform) γ's (ppm) at .95 (doublet), 1.66 (doublet), 2.61, 2.76, 3.28 (multiplet), 3.60, 3.70, 3.81, 3.85, 4.09 (multiplet), 5.47 (multiplet), 5.80 (ethylenic hydrogens), 6.10, 6.57. Mass spectrograph: Molecular ion at 750, other peaks at 692, 691, 633, 620, 553, 525, 524, 427, 337, 336, 240, 171, 167, 149, 136, 135, 122, and transmethylation peaks at 764 and 778.

4',20'-Anhydro C-4-desacetyl-VLB isomer 2 (z is IIIc) 22.5 mg. with the following physical characteristics: (Partial) NMR spectrum (deuterated chloroform) γ's (ppm) at .95 (doublet), 1.71 (doublet), 2.60, 2.75 (N-methyl), 3.25 (multiplet), 3.60 (ester), 3.79, 3.84, 4.08 (multiplet), 5.28 (multiplet), 5.80 (ethylenic hydrogens), 6.08, 6.55. Mass spectrograph: Molecular ion at 750; other peaks at 691, 633, 620, 553, 525, 427, 337, 336, 240, 171, 167, 149, 136, 135, 122, 121, 107, 106, and transmethylation peaks at 764 and 778.

EXAMPLE 3

ANHYDRO COMPOUNDS FROM LEUROSIDINE

Following the procedure of Example 1, 162.2 mg. of leurosidine were added slowly to 1.9391 g. of cold 18M sulfuric acid. The reaction was carried out and the mixture of the three anhydro derivatives obtained as set forth in that Example. The mixture of the three anhydro leurosidine derivatives was separated by preparative thin layer chromatography to yield purified fractions of the identical anhydro derivatives as obtained above from VLB.

Also prepared by the procedure of Example 1 were three anhydro derivatives of C-4 desacetyl VLB C-3 carboxamide (Formula II in which R is NH$_2$, R' is OH, R'' is methyl, and Z is IIIa, b, and c). These three derivatives were designated as the 3',4'-anhydro C-4 desacetyl VLB C-3 carboxamide, 4'20'-anhydro C-4 desacetyl VLB C-3 carboxamide-isomer 1 (Z equals IIIb) and the other isomer, isomer 2 (Z equals IIIc).

Each of the above C-4 desacetyl derivatives can be reacetylated by the procedure of Hargrove Lloydia, 27 340 (1964), to yield compounds according to Formula II in which R' is acetoxy.

Other compounds of this invention preparable by the above procedures include 3',4'-anhydro vincristine C-3-carboxamide, 4',20'-anhydro vincristine C-3 carboxamide (isomers 1 and 2); 3',4'-anhydro C-4 desacetyl VLB C-3 carboxyhydrazine, 4',20'-anhydro C-4 desacetyl VLB C-3 carboxyhydrazide (isomers 1 and 2); 3',4'-anhydro C-4 desacetyl vincristine C-3 N- methylcarboxyamide, 4',20'-anhydro C-4 desacetyl vincristine C-3 N-methylcarboxamide (isomers 1 and 2); 3',4'-anhydro VLB C-3 carboxamide, 4',20'-anhydro VLB C-3 carboxamide (isomers 1 and 2), and the like.

The compounds of this invention are active as mitotic inhibitors as shown by their ability to arrest cultured cells at the mitotic phase (metaphase) of the cell cycle without apparent affect on other stages of the cell cycle. The compounds also show activity against Ridgeway osteogenic Sarcoma, adenosarcoma 755, P 1534 leukemia, B-16 melanoma and Gardner lymphosarcoma in mice. Most of the known anti-tumor indole-dihydroindole (dimeric) alkaloids from *Vinca rosea* have the ability to cause metaphase arrest including VLB, leurosidine and vincristine. Monomeric Vinca alkaloids do not possess metaphase arrest activity and are not antimitotics. The following table gives the results of antimitotic testing of the compounds coming within the scope of Formula II above. In the table, column 1 gives the name of the compound and column 2 the mitotic index, minimum concentration for 50 percent arrest.

Table

| Compound Name | Mitotic Index: Minimum Concentration For 50 Percent Arrest in mcg./ml. |
|---|---|
| 3',4'-anhydro C-4-desacetyl VLB | $2 \times 10^{-2} \pm$ |
| 4',20'-anhydro C-4-desacetyl VLB- (isomer 2) | $2 \times 10^{-1}$ and $2 \times 10^{-2} \pm$ |
| 4',20'-anhydro C-4-desacetyl VLB- (isomer 1) | $2 \times 10^{-2} +$ |
| 3',4'-anhydro C-4-desacetyl vincristine | $2 \times 10^{-2} \pm$ |
| 4',20'-anhydro C-4-desacetyl vincristine (isomer 2) | $2 \times 10^{-1} +$ |
| 4',20-anhydro C-4-desacetyl vincristine (isomer 1) | $2 \times 10^{-3} \pm$ $2 \times 10^{-2} ++$ |
| 3',4'-anhydro C-4-desacetyl VLB C-3 carboxamide | $2 \times 10^{-1} +$ |
| 4',20'-anhydro C-4-desacetyl VLB C-3 carboxamide (isomer 1) | $2 \times 10^{-2} +$ |
| 4',20'-anhydro C-4-desacetyl VLB C-3 carboxamide (isomer 2) | $2 \times 10^{-2} +$ |

In the above tests, VLB has a mitotic index $2 \times 10^{-2}$ ++, vincristine $2 \times 10^{-3} \pm$, and C-4 desacetyl vincristine, $2 \times 10^{-3}$ ++.

We claim:
1. The compound represented by the formula

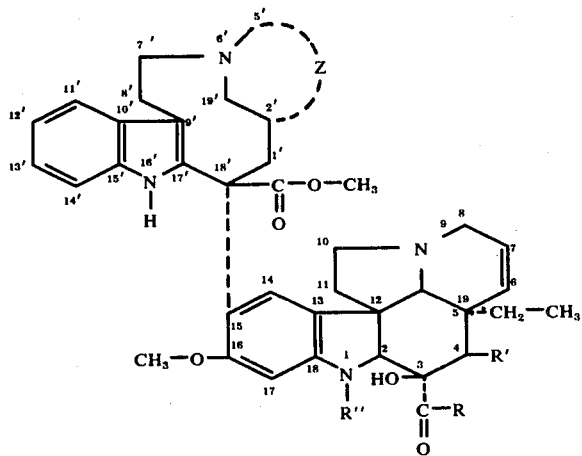

wherein R is OCH$_3$, NH$_2$, NHCH$_3$, NHC$_2$H$_5$, NH—C$_2$H$_4$OH or NH—NH$_2$; R" is CH$_3$, H, or formyl; R' is hydroxy or acetoxy and Z is

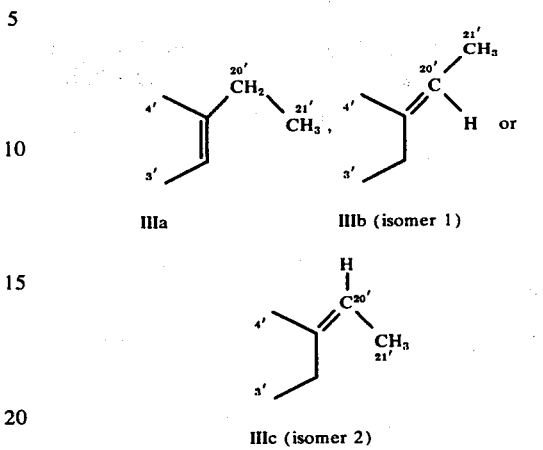

IIIa     IIIb (isomer 1)

IIIc (isomer 2)

2. The compound according to claim 1, said compound being 3',4'-anhydro C-4 desacetyl vincristine.

3. The compound according to claim 1, said compound being 4',20'-anhydro C-4 desacetyl vincristine (isomer 1)

4. The compound according to claim 1, said compound being 4',20'-anhydro C-4 desacetyl vincristine (isomer 2).

5. The compound according to claim 1, said compound being 3',4'-anhydro C-4 desacetyl VLB.

6. The compound according to claim 1, said compound being 4',20'-anhydro C-4 desacetyl VLB (isomer 1).

7. The compound according to claim 1, said compound being 4',20'-anhydro C-4 desacetyl VLB (isomer 2).

8. The process which comprises the step of contacting a compound of the formula

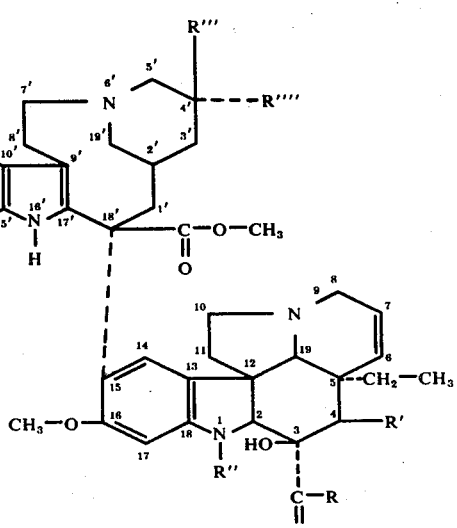

wherein R is OCH$_3$, NH$_2$, NH—NH$_2$, NHC$_2$H$_5$ NH—C$_2$H$_4$OH or NHCH$_3$, NHC$_2$H$_5$, NH—C$_2$H$_4$OH R' is OH or

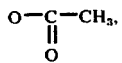
R'' is CH₃H or CHO, and one of R''' and R'''' is ethyl, the other being hydroxy, with cold concentrated sulfuric acid to form a compound of the formula
II
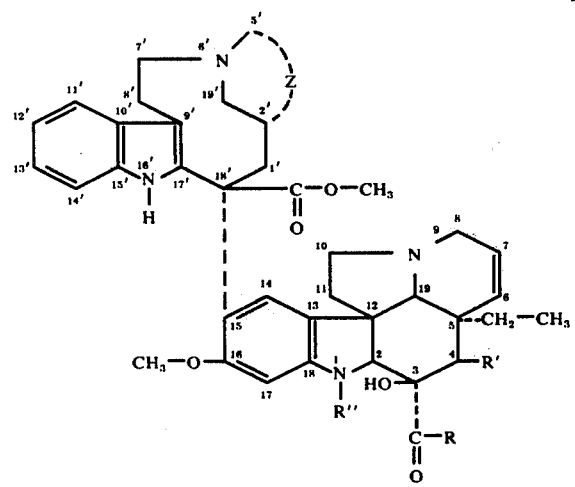
wherein R is OCH₃, NH₂, NHCH₃, or NH-NH₂; R'' is CH₃ or CHO; R' is hydroxy and Z is
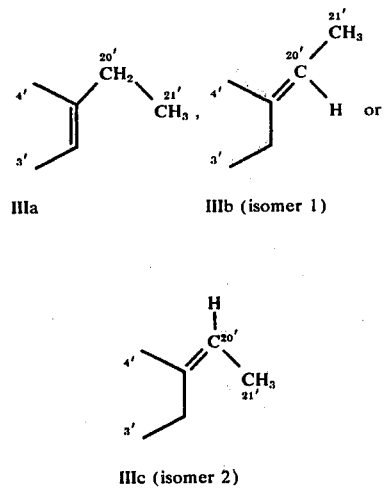
* * * * *